United States Patent [19]
Vogt

[11] Patent Number: 5,435,721
[45] Date of Patent: Jul. 25, 1995

[54] ORTHODONTIC DEVICE

[76] Inventor: William Vogt, R.D. 4, Box 4205, Bangor, Pa. 18013

[21] Appl. No.: 196,437

[22] Filed: Feb. 15, 1994

[51] Int. Cl.$^6$ .......................................... A61C 3/00
[52] U.S. Cl. .................................... 433/19; 433/18
[58] Field of Search .................. 433/18, 19, 21, 22

[56] References Cited

U.S. PATENT DOCUMENTS

| | | |
|---|---|---|
| 741,687 | 10/1903 | MacDowell . |
| 3,121,953 | 2/1964 | Asher . |
| 3,137,941 | 6/1964 | Andrews . |
| 3,315,359 | 4/1967 | Moss . |
| 3,618,214 | 11/1971 | Armstrong .............. 433/19 |
| 3,798,773 | 3/1974 | Northcutt . |
| 3,803,715 | 4/1974 | Wallshein .............. 433/18 |
| 3,997,970 | 12/1976 | Hodgson . |
| 4,382,782 | 5/1983 | Klein et al. .............. 433/18 |
| 4,439,149 | 3/1984 | Devincenzo . |
| 4,462,800 | 7/1984 | Jones .............. 433/19 |
| 4,551,095 | 11/1985 | Mason .............. 433/19 |
| 4,708,646 | 11/1987 | Jasper .............. 433/19 |
| 4,795,342 | 1/1989 | Jones .............. 433/19 |
| 4,849,032 | 7/1989 | Kawaguchi .............. 433/21 |
| 5,022,855 | 6/1991 | Jeckel .............. 433/18 |
| 5,074,784 | 12/1991 | Sterrett et al. .............. 433/18 |
| 5,167,499 | 12/1992 | Arndt et al. .............. 433/18 |
| 5,183,388 | 2/1993 | Kumar .............. 433/19 |
| 5,302,117 | 4/1994 | Kraut et al. .............. 433/18 |
| 5,312,247 | 5/1994 | Sachdeva et al. .............. 433/18 |

FOREIGN PATENT DOCUMENTS 0230394 7/1987 European Pat. Off. .............. 433/18

*Primary Examiner*—Cary E. O'Connor
*Attorney, Agent, or Firm*—Weiser & Associates

[57] ABSTRACT

An orthodontic appliance having improved devices for interconnecting the braces associated with a patient's upper and lower teeth. Each connecting device generally takes the form of a unitary, thin band of material that can be connected between the braces associated with the patient's upper and lower teeth to achieve the forces that are desired for a particular treatment. The connecting device has a body that is substantially flat and rectangular, with bent end portions that are preferably rounded for purposes of comfort. Each end portion includes an aperture for attachment to the braces associated with the patient's teeth. Preferably, at least one of the apertures of each connecting device is keyed so that upon its attachment to the braces, swivelling of the connecting device is effectively precluded without compromising desired movements of the connecting device relative to the orthodontic appliance and the patient's mouth. As a result, interaction between the connecting devices and the patient's jaws, lips and cheeks is minimized, and breakage is effectively precluded. The connecting device is capable of being formed of a material that can produce forces, upon use of the connecting device, that are sufficiently small to produce desired movements of the teeth without producing undesired movements of the patient's jaws.

35 Claims, 3 Drawing Sheets

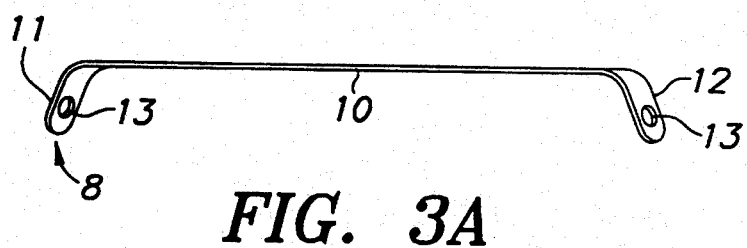
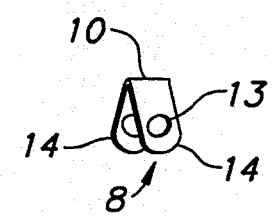
FIG. 3A  FIG. 5A
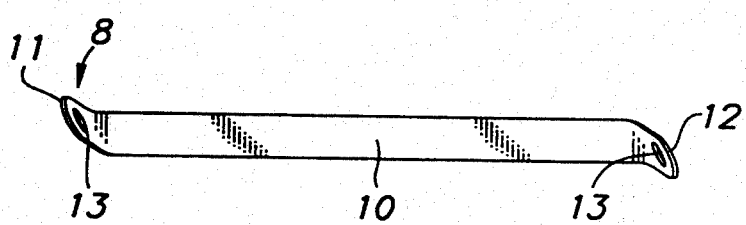
FIG. 4A
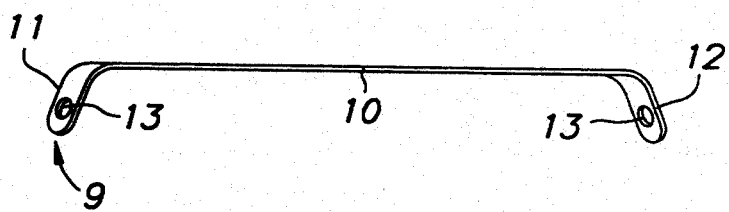
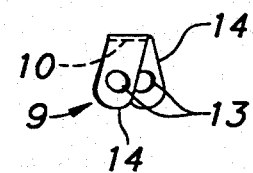
FIG. 3B  FIG. 5B
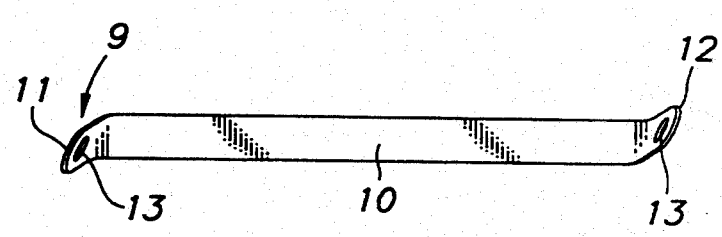
FIG. 4B

ORTHODONTIC DEVICE

BACKGROUND OF THE INVENTION

The present invention relates generally to orthodontic devices for treating various malocclusions including protrusion and retrusion of the upper teeth relative to the lower teeth, and misalignments of the teeth relative to one another.

A variety of malocclusions have been corrected with conventionally available orthodontic appliances for achieving realignments of the teeth so that an appropriate alignment is established for the upper teeth, for the lower teeth, and between the upper and lower teeth. Early efforts involved the application of orthodontic appliances to the teeth in conjunction with elastic (rubber) bands to apply appropriate forces to the orthodontic appliance and, as a result, to the teeth, as well as removable head gear for interacting with the teeth, to achieve desired movements. Although these techniques have provided satisfactory results, they were found to be subject to certain disadvantages.

The greatest disadvantage of such orthodontic systems is that satisfactory results can only be obtained if a particular device is properly worn. Elastic bands and head gear are rather easily removed by the patient, at times limiting their overall effectiveness. Head gear has the further disadvantage that since the neck), it is cosmetically undesirable and therefore less likely to be properly worn.

Another disadvantage of such orthodontic systems is that they can produce undesirable side effects resulting from undesirable forces that may come to be applied to the orthodontic appliance in addition to those forces which are desired for an effective treatment to take place. These undesirable forces are most prevalent for elastic bands, at times resulting in tooth extrusion and bite opening. Head gear can also result in tooth extrusion. Elastic bands further have the disadvantage of delivering forces that can decay over time, as the elastic elements stretch and fatigue.

Various devices have been developed in an effort to improve upon the elastic bands and head gear of conventional orthodontic appliances. One such attempt involves the use of spring operated devices, primarily to replace the elastic bands. Such devices are disclosed, for example, in U.S. Pat. Nos. 3,618,214 (Armstrong), 4,795,342 (Jones), 5,022,855 (Jeckel) and 5,074,784 (Sterrett et al).

Generally speaking, such devices employ springs to establish tensions similar to those formerly established by elastic bands. However, in practice, it has been found that such devices tend to produce relatively severe and undesirable side effects leading to unwanted tooth extrusion and bite opening. Moreover, most available spring-operated devices are themselves removable (much like the elastic bands they replace), and are often either not worn, lost or broken. For those spring-operated devices that are removable, a common requirement is for the patient to remove the device to eat or to brush the teeth. For those spring-operating devices that are not removable, it is often extremely difficult to clean around such devices. In either case, such devices tend to be bulky, making it difficult for patients to talk with the appliances in place.

Another orthodontic device that has recently found increased acceptance is the so-called "bite jumping" appliance. Such appliances are disclosed, for example, in U.S. Pat. Nos. 3,798,773 (Northcutt), 4,462,800 (Jones), 4,551,095 (Mason), 4,708,646 (Jasper) and 5,183,388 (Kumar).

All except U.S. Pat. No. 4,708,646 disclose variations of a device generally known as the "Herbst" device, and include a metal cylinder containing a plunger and attachable to and between the orthodontic appliances (braces) fixed to the patient's upper and lower teeth. Such devices are rigidly attached to the associated orthodontic appliances and, as a result, cannot be removed by the patient. However, because of their rigid attachment, it is not uncommon for such devices to become damaged, or to cause damage to the orthodontic appliances to which they are attached. Primarily, this results from the lack of flexibility of such devices, and the relatively large forces that can be produced as the patient's jaws are closed (in the normal course).

U.S. Pat. No. 4,708,646 replaces the more conventional Herbst device with an elastic element comprised of a spring surrounded by a rubber core and having metal end caps for attachment to and between the orthodontic appliances associated with the patient's upper and lower teeth. In use, the disclosed elastic element tends to produce extremely high forces, similar to the Herbst device, and is highly susceptible to breakage. Breakage primarily results from the ability of such a device to swivel about its attachment points, producing significant flexure and permitting the device to at times become caught between the patient's upper and lower teeth (and chewed upon). Separation of the end caps from the connecting spring and cover is quite common as a result.

Also to consider is that such devices are primarily directed toward the treatment of retrusion of the lower jaw. Such appliances are not generally useful in treating malocclusions of the teeth that are not related to underlying skeletal defects (such as misalignment of the jaw). The reason for this is that favorable tooth movement is difficult to achieve in view of the relatively heavy forces that are produced by such devices. Because of this, the use of such devices can be disadvantageous when the patient has upper and lower jaws that are correctly aligned, and only movement of the patient's teeth is required (either relative to one another, or relative movement of the upper teeth and the lower teeth). As a result, such appliances can only be used in limited situations.

Consequently, the need remains to provide a device for developing the forces that are appropriate toward effectively interconnecting orthodontic appliances to achieve the movements that are desired for a particular treatment, and which are less subject to the disadvantages of non-use and breakage.

SUMMARY OF THE INVENTION

It is therefore the primary object of the present invention to provide an improved orthodontic appliance.

It is also an object of the present invention to provide an improved orthodontic appliance for the treatment of dental malocclusions including protrusion or retrusion of the upper teeth relative to the lower teeth, and misalignments of the teeth relative to one another.

It is also an object of the present invention to provide an orthodontic appliance having connectors that are less susceptible to breakage, and to damage of the orthodontic appliance with which they are used.

It is also an object of the present invention to provide an orthodontic appliance that can produce forces sufficiently small to effectively realign the teeth without adverse side effects such as concurrent movement of the jaws relative to one another.

It is also an object of the present invention to provide an orthodontic appliance that is sufficiently resilient, and which provides a sufficient degree of movement to achieve desired orthodontic treatments.

It is also an object of the present invention to provide an orthodontic appliance having characteristics that promote its being worn by the patient.

It is also an object of the present invention to provide an orthodontic appliance that is comfortable to wear, unobtrusive and cosmetically acceptable.

It is also an object of the present invention to provide an orthodontic appliance that can provide relatively consistent forces throughout a desired orthodontic procedure.

It is also an object of the present invention to provide an orthodontic appliance which is simple in construction, and easy to install and adjust.

These and other objects which will become apparent are achieved in accordance with the present invention by providing an orthodontic appliance having improved devices for interconnecting the braces associated with a patient's upper and lower teeth. Each connecting device generally takes the form of a unitary, thin band of material that can be connected between the braces associated with the patient's upper and lower teeth to achieve the forces that are desired for a particular treatment. The connecting device has a body that is substantially flat and rectangular, with bent end portions that are preferably rounded for purposes of comfort. Each end portion includes an aperture for attachment to the braces associated with the patient's teeth. Preferably, at least one of the apertures of each connecting device is keyed so that upon its attachment to the braces, swivelling of the connecting device is effectively precluded without compromising desired movements of the connecting device relative to the orthodontic appliance and the patient's mouth. As a result, interaction between the connecting devices and the patient's jaws, lips and cheeks is minimized, and breakage is effectively precluded. The connecting device is capable of being formed of a material that can produce forces, upon use of the connecting device, that are sufficiently small to produce desired movements of the teeth without producing undesired movements of the patient's jaws.

For further detail, reference is made to the detailed description which is provided below, taken in conjunction with the following illustrations.

BRIEF DESCRIPTION OF THE DRAWINGS

FIGS. 3A and 3B are side elevational views showing connecting devices for association with the left and right sides of the orthodontic appliance, respectively.

FIGS. 4A and 4B are top plan views of the connecting devices of FIGS. 3A and 3B, respectively.

FIGS. 5A and 5B are end views of the connecting devices of FIGS. 3A and 3B, respectively.

In the several views provided, like reference numbers denote similar structure.

DETAILED DESCRIPTION OF PREFERRED EMBODIMENTS

Figure 1:
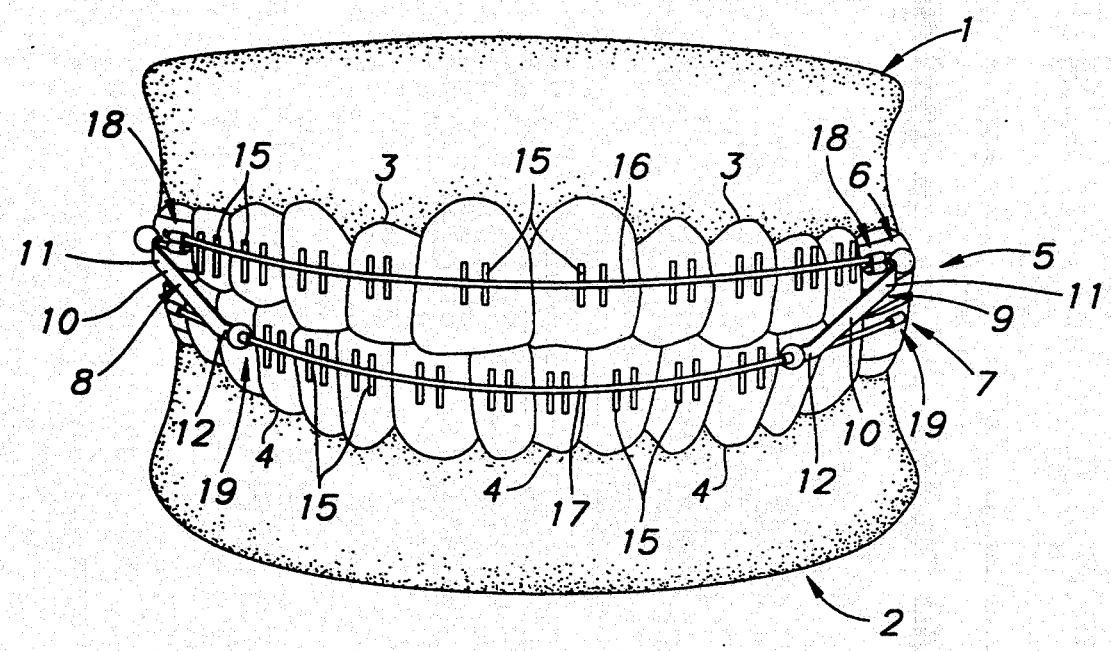
FIG. 1 is an elevational view showing an orthodontic appliance incorporating connecting devices of the present invention, as viewed from the front of the patient's mouth.
Figure 2:
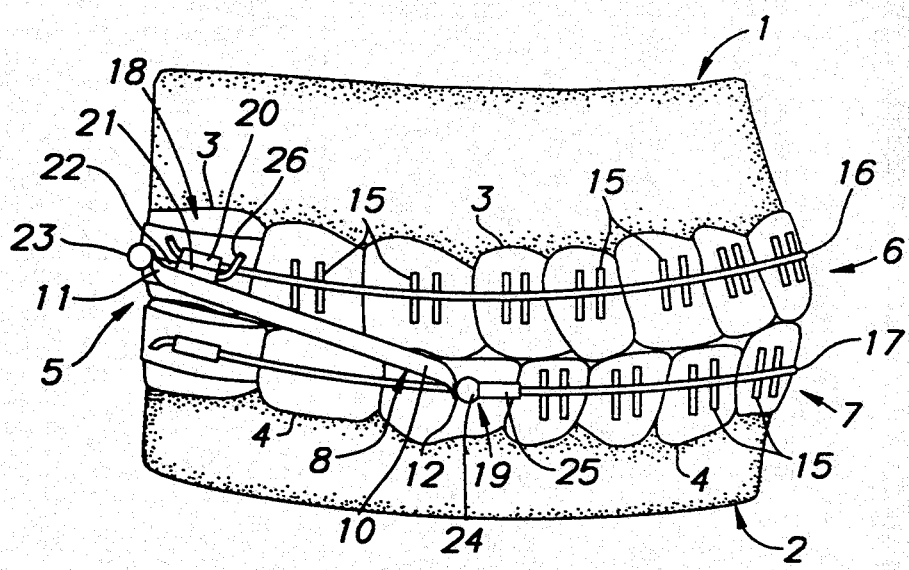
FIG. 2 is an elevational view showing an orthodontic appliance incorporating connecting devices of the present invention, as viewed from the side of the patient's mouth.

FIGS. 1 and 2 illustrate the upper jaw 1 and the lower jaw 2 of a hypothetical patient. Upper teeth 3 are associated with the upper jaw 1 and lower teeth 4 are associated with the lower jaw 2. An orthodontic appliance 5 is applied to and between the upper and lower teeth 3, 4 to achieve desired movements of the upper teeth 3 and/or the lower teeth 4 relative to each other. While it would also be possible to achieve movements of the upper jaw 1 and the lower jaw 2 relative to each other, the discussion which follows is primarily directed toward relative movements of the upper teeth 3 and the lower teeth 4 without associated movements of the upper jaw 1 and the lower jaw 2, as well as to movements of either the upper teeth 3 or the lower teeth 4 relative to one another. However, it is to be understood that the improvements of the present invention are applicable to any of a number of orthodontic procedures other than those which will be specifically described below. Such orthodontic procedures will be readily understood by the person of ordinary skill in the art, and are achievable by causing the various elements of the orthodontic appliance 5 to interact with the teeth 3, 4, and if desired, the jaws 1, 2, employing techniques that are themselves known and conventional.

The orthodontic appliance 5 is generally comprised of an upper appliance 6 associated with the upper teeth 3, a lower appliance 7 associated with the lower teeth 4, and in the illustrative embodiment shown in FIGS. 1 and 2, a pair of connecting devices 8, 9 interconnecting the upper appliance 6 and the lower appliance 7. The connecting device 8 extends between left-most portions of the upper appliance 6 and left-most portions of the lower appliance 7, while the connecting device 9 extends between right-most portions of the upper appliance 6 and right-most portions of the lower appliance 7. Specifics regarding such attachment will be discussed more fully below.

Construction of the connecting devices 8, 9 is best understood with reference to FIGS. 3A, 4A and 5A, which illustrate the connecting device 8 associated with the left-most portions of the orthodontic appliance 5, and FIGS. 3B, 4B and 5B, which illustrate the connecting device 9 associated with the right-most portions of the orthodontic appliance 5. Overall construction Of the connecting devices 8, 9 is substantially the same, except that the connecting device 8 substantially constitutes a mirror image of the connecting device 9. This is necessary for proper interaction of the connecting devices 8, 9 with the upper and lower appliances 6, 7, as will be discussed more fully below.

Each of the connecting devices 8, 9 is formed as a flat, substantially rectangular plate 10 having end portions 11, 12 for attachment to and between the upper and lower appliances 6, 7, respectively. Each of the end portions 11, 12 is formed as an integral portion of the plate 10, so that each of the connecting devices 8, 9 is unitary in construction. This is advantageously accomplished with flat plate materials sized to include the plate 10 and end portions 11, 12. The end portions 11, 12 can then be bent (preferably, a gradual bend) relative to the plate 10 to form the desired connecting device. Each of the end portions 11, 12 includes an aperture 13 for attachment to the upper and lower appliances 6, 7, and is preferably rounded (shown at 14) to avoid sharp edges that could irritate and possibly injure the patient's jaws, teeth, lips and cheeks.

The configuration of the connecting devices 8, 9 can be varied, as desired, to suit the requirements of a particular application. Preferably, connecting devices of different sizes will be produced to accommodate variations in the size of the patient's jaws 1, 2, and the associated teeth 3, 4, as well as the particular orthodontic procedure to be accomplished. The following parameters are given by way of illustration. The connecting devices 8, 9 will preferably have lengths of from 22 mm to 38 mm. Variations in length having increments of 2 mm should be sufficient for most purposes. The connecting devices 8, 9 will preferably have widths of from 3 mm to 9 mm. A width of about 5 mm is presently considered to be preferable in most cases. The unitary element forming the plate 10 and the end portions 11, 12 will preferably have a thickness of from 0.010 inches to 0.090 inches.

Different amounts of force can be achieved, primarily responsive to variations in the above parameters and the materials used to form the connecting devices 8, 9. In terms of the above-mentioned parameters, variations in width and/or thickness will primarily determine the forces that are produced by the connecting devices 8, 9. Of course, the comfort of the patient needs to be taken into consideration as well. Preferred materials for forming the connecting devices 8, 9 presently include spring stainless steel, titanium, nickel-titanium (including super-elastic nickel-titanium) and carbon fiber resins. However, other materials can also be used to produce the forces that are desired, provided the selected material is inert when present in the mouth of a patient. The selected material can, if desired, be provided with a protective coating (e.g., plastic or rubber) to either ensure its inert behavior inside the patient's mouth, or for purposes of comfort and/or safety (the applied coating can even serve to entrain broken portions of the connecting device in the event of a failure) In any event, it is important that the material selected for use in producing the connecting devices 8, 9 have sufficient elasticity to be safe and comfortable when worn by the patient, and sufficient resiliency to produce the forces that are desired, and to recover their initial shape following the twisting and bending that will occur when associated with the orthodontic appliance 5.

Shaping of the end portions 11, 12 will vary not only in accordance with the orthodontic treatment that is intended, but also in accordance with the side of the patient's mouth that is to receive the connecting device. For example, to ensure that proper forces are developed, while maximizing patient comfort, it will be noted that the end portions 11, 12 of the connecting devices 8, 9 are formed so that the end portions 11, 12 depend from the associated appliances 6, 7, causing the plate 10 to lie between the appliances 6, 7. This tends to minimize extension of the connecting devices 8, 9 above the upper appliance 6 and below the lower appliance 7, or outwardly from the appliances 6, 7. For this reason, the end portions 11, 12 are preferably angled relative to the plate 10 so that the end portions 11, 12 (as well as their seam with the plate 10) will be substantially vertically oriented when associated with the orthodontic appliance 5.

To accomplish this, the end portions 11, 12 of the left-most connecting device 8 are preferably bent relative to the plate 10 so that each end portion forms an angle of 0 to 120 degrees (preferably, of about 60 degrees) and includes a twist of 0 to 90 degrees (preferably, of about 45 degrees) The end portions 11, 12 of the right-most connecting device 9 are preferably bent relative to the plate 10 so that each end portion forms an angle of 0 to 120 degrees (preferably, of about 60 degrees) and includes a twist of 270 to 0 degrees (preferably, of about 315 degrees). Employing parameters such as these will produce connecting devices 8, 9 similar to those shown in FIGS. 3A, 3B, 4A and 4B, with the offset end portions 11, 12 that are best shown in FIGS. 5A and 5B.

If appropriate for a particular orthodontic procedure, the apertures 13 of the end portions 11, 12 may be round, for engaging conventional connecting wires associated with the orthodontic appliance. However, in accordance with the present invention it has been found to be particularly advantageous to provide the connecting devices 8, 9 with apertures 13 that are in essence "keyed" to the connecting wires of the orthodontic appliance.

In particular, it has been found that swiveling of the connecting devices 8, 9 relative to the upper and lower appliances 6, 7 can be prevented by appropriately shaping the apertures 13 to engage shaped connecting wires (of the appliances 6, 7 that are to receive them). As an example, the apertures 13 can be squared, for interacting with squared connecting wires associated with the orthodontic appliance 5. Any of a variety of shapes (polygonal, regular, irregular, etc.) can be used to achieve a similar function. If desired, the apertures 13 associated with each of the end portions 11, 12 of a particular connecting device may be shaped for interacting with the connecting wires of the orthodontic appliance 5. However, in many applications it will be sufficient to provide only one of the apertures 13 (associated with either the end portion 11 or the end portion 12) with a shaped configuration for interaction with the connecting wire of either the upper appliance 6 or the lower appliance 7, as desired. The apertures 13 associated with a particular connecting device 8, 9 can either be the same, or different in shape, depending upon preference and the orthodontic procedure to be performed.

Keying the apertures 13 of the connecting devices 8, 9 can also serve to ensure that the connecting device 8 is properly associated with the left-most portions of the orthodontic appliance 5 and that the connecting device 9 is correctly associated with the right-most portions of the orthodontic appliance 5. This could also be accomplished by marking the connecting devices 8, 9. However, keying the apertures 13 of the connecting devices 8, 9 has the added advantage of automatically ensuring that the connecting devices 8, 9 are properly associated with the orthodontic appliance 5. A similar result is also obtainable by providing the apertures 13 of the connecting devices 8, 9 to be associated with the upper appliance 6 with a size (e.g., diameter) that differs from the size of the apertures 13 of the connecting devices 8, 9 to be associated with the lower appliance 7.

The apertures 13 are capable of variation, both in terms of their size and their shape. However, for most applications, round apertures 13 having diameters of from 1 to 4 mm (and preferably 2 mm) should be sufficient. For rectangular (keyed) apertures 13, lengths of from 0.021 to 0.1 inches and widths of from 0.017 to 0.026 inches are presently preferred. The apertures 13 associated with the ends 11, 12 of the connecting devices 8, 9 may be similar in terms of their size and shape, or dissimilar, as desired. While the apertures 13 are preferably symmetrically positioned in the end portions 11, 12, other (offset) positionings may be provided for different applications, if desired.

Referring again to FIGS. 1 and 2, attachment of the connecting devices 8, 9 to the upper and lower appliances 6, 7 (completing the orthodontic appliance 5) will now be described for the illustrative procedure that is shown. In substantially conventional fashion, the upper appliance 6 is attached to the upper teeth 3 by attaching (e.g., gluing or bonding) a plurality of supports 15 to the upper teeth 3, and by appropriately interconnecting the supports 15 with a common wire 16. The lower appliance 7 is similarly attached to the lower teeth 4 by affixing a plurality of supports 15 to the lower teeth 4, and by interconnecting the supports 15 with a common wire 17. To this point, the procedure involved is substantially conventional, and could employ any of a variety of known techniques to accomplish the desired end result.

The connecting devices 8, 9 are then attached to and between the appliances 6, 7, making sure to fit the connecting device 8 to the left-most portions of the orthodontic appliance 5 and the connecting device 9 to the right-most portions of the orthodontic appliance 5. To this end, and for each of the connecting devices 8, 9, the upper appliance 6 is provided with a connector 18 and the lower appliance 7 is provided with a connector 19 for receiving the end portions 11, 12 of the connecting devices 8, 9.

In this illustrative embodiment, the connector 18 includes a tube 20 for slidingly receiving an end of the wire 16 and a tube 21 connected to the tube 20, for receiving a connecting wire 22. The terminating end of the connecting wire 22 includes a ball stop 23, which is preferably integral with the connecting wire 22. The connector 19 employs the wire 17 of the lower appliance 7, in combination with a ball 24 (which bears against a crimpable stop 25 for slidingly receiving the wire 17) associated with the wire 17. Of course, any of a variety of known connectors may be employed, apart from the connectors 18, 19, if desired.

Upon assembly, the aperture 13 of the end portion 12 is engaged by the wire 17 (the connector 19) of the lower appliance 7 and the aperture 13 of the end portion 11 is engaged by the connecting wire 22 (the connector 18) associated with the upper appliance 6. The connecting wire 22 is then bent over, at 26, finishing the desired assembly.

Resulting from such assembly, the connecting devices 8, 9 are appropriately positioned between the connector 18 of the upper appliance 6 and the connector 19 of the lower appliance 7 so that upon closure of the jaws 1, 2, the balls 23, 24 will interact with the end portions 11, 12 of the connecting devices 8, 9, developing the compressive forces that are desired (in this case, between the upper molar area and the lower canine area) for appropriate tooth movement (e.g., in a mesial or distal direction). As the jaws 1, 2 are opened, the end portions 11, 12 are permitted to slide along the associated wires 17, 22, permitting the jaws 1, 2 to open freely. The length of the connecting devices 8, 9 will be selected so that upon closure of the jaws 1, 2, interaction between the balls 23, 24 and the connecting devices 8, 9 will urge the upper teeth 3 inwardly relative to the lower teeth 4, achieving the desired realignment over time.

Figure 6:
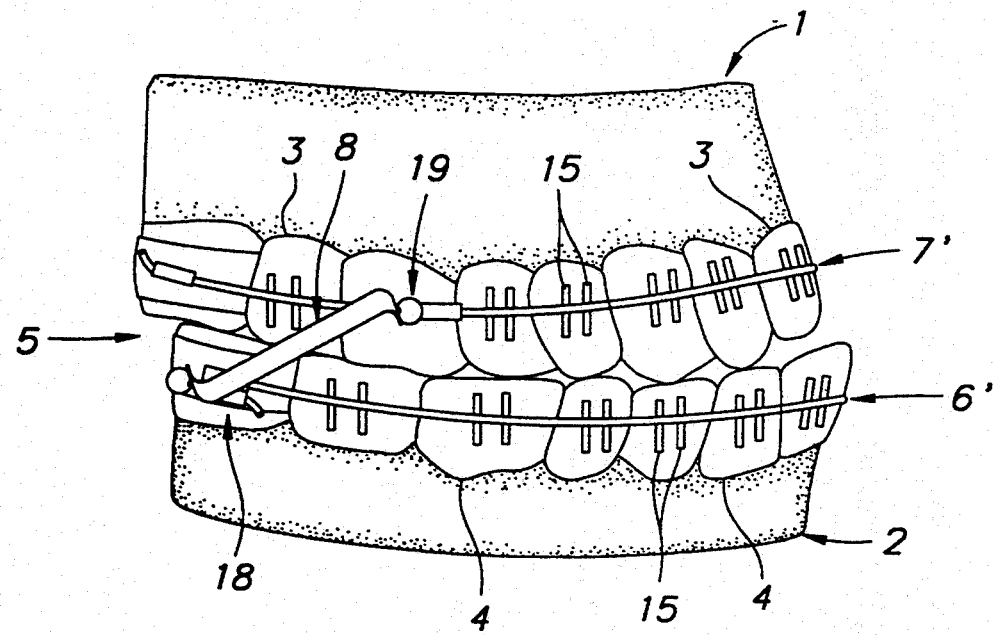
FIGS. 6 and 7 are elevational views similar to FIG. 2, showing alternative embodiment orthodontic appliances incorporating connecting devices of the present invention.

Referring to FIG. 6, the upper teeth 3 can be urged outwardly relative to the lower teeth 4 by reversing the appliances 6, 7 so that the appliance 6' is associate with the lower teeth 4 and so that the appliance 7' is associated with the upper teeth 3. All other attachment procedures will remain substantially the same.

Figure 7:
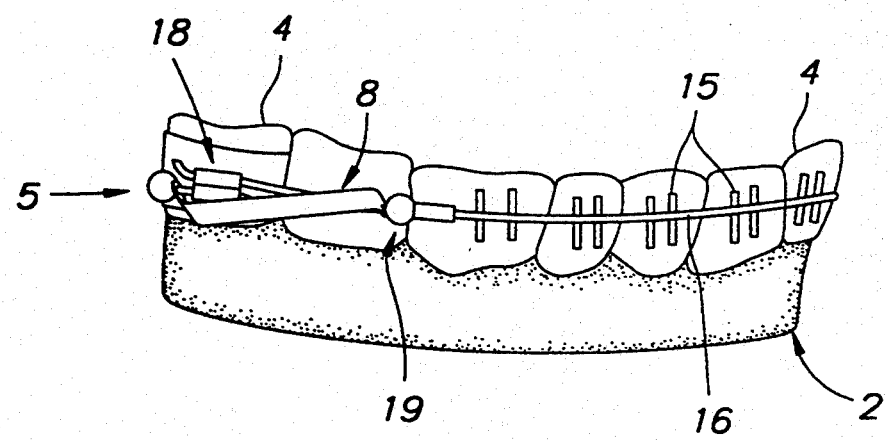

Referring to FIG. 7, it is also possible to provide either (or both) of the appliances 6, 7 (depending upon whether the upper teeth 3 or the lower teeth 4 are to be operated upon) with both a connector 18 and a connector 19, and to fit the connecting devices 8, 9 between the connectors 18, 19. The connecting devices 8, 9 can in this way operate as an intra-arch spring, by applying compressive forces between the connectors 18, 19 which can serve to separate teeth of either the upper jaw 1 or the lower jaw 2 (or both) from one another. Because relatively light forces can be produced by the connecting devices 8, 9, orthodontic appliances such as those illustrated in FIGS. 1, 2 and 6 can also be effectively used to provide an increased spacing of the teeth (i.e., enlargement of the jaw), if desired for a particular orthodontic procedure.

Any of a variety of orthodontic procedures may be performed using techniques similar to those described above. To be noted is that irrespective of the orthodontic procedure to be performed, and the orthodontic appliance that is formed in accordance with the present invention, the connecting devices 8, 9 are caused to interact with the appliances 6, 7 so that the end portions 11, 12 can slide along the associated wires 17, 22, respectively. The connecting devices 8, 9 are permitted to pivot from side to side, and up and down, to provide desired freedom of movement during normal oral function. Generally, this will be accomplished while preventing the connecting devices 8, 9 from swiveling relative to the appliances 6, 7, to reduce the potential for breakage (of the connecting devices 8, 9 or at the connectors 18, 19) and to prevent irritation and/or injury to the adjoining lips and cheeks of the patient. To this end, either the end portion 11, the end portion 12 or both end portions 11, 12 would preferably include keyed apertures 13, as previously described.

The foregoing improvements are achieved making use of connecting devices 8, 9 that are formed from flat, plate materials. In addition to their ease of manufacture, such materials are less subject to the fatigue previously encountered with elastic bands, ensuring that the forces applied by the connecting devices 8, 9 are substantially constant over time, as is desired. The amount of force (activation) achievable by means of the connecting devices 8, 9 can be varied either by adjusting the characteristics of the connecting devices 8, 9 as previously described, or by providing the connector 19 with plural stops instead of the single fixed stop (i.e., the crimpable stop 25) employed in conjunction with the illustrated orthodontic appliance 5.

It will therefore be understood that various changes in the details, materials and arrangement of parts which have been herein described and illustrated in order to explain the nature of this invention may be made by those skilled in the art within the principal and scope of the invention as expressed in the following claims.

What is claimed is:

1. A unitary element in combination with a first appliance of an orthodontic device attached to first teeth associated with a first jaw of a patient, and a second appliance of the orthodontic device attached to second teeth associated with a second jaw of the patient, wherein the first appliance and the second appliance are capable of association with the teeth of the patient for applying forces to and between the first appliance and the second appliance, and the teeth associated with the first appliance and the second appliance, wherein the connecting element includes a body portion having integral end portions for attachment to and between the first appliance and the second appliance, for developing forces between the first appliance and the second appliance and for moving the first teeth relative to the second teeth, and wherein the connecting element is formed of an elastic material having sufficient resiliency to maintain shape and develop forces between the end portions of the connecting element.

2. The connecting element of claim 1 wherein the body portion and the integral end portions are formed from a substantially flat plate.

3. The connecting element of claim 2 wherein the flat plate is formed of a material selected from the group consisting of spring stainless steel, titanium, nickel-titanium, super-elastic nickel-titanium and carbon fiber resin.

4. The connecting element of claim 2 wherein the flat plate has a length of from 22 mm to 38 mm.

5. The connecting element of claim 4 wherein a plurality of flat plates have lengths which vary in increments of 2 mm.

6. The connecting element of claim 2 wherein the flat plate has a width of from 3 mm to 9 mm.

7. The connecting element of claim 6 wherein the width is about 5 mm.

8. The connecting element of claim 2 wherein the flat plate has a thickness of from 0.010 inches to 0.090 inches.

9. The connecting element of claim 2 wherein the end portions are formed at an angle relative to the body portion.

10. The connecting element of claim 9 wherein the body portion defines a plane, and wherein the end portions form an angle of from 0 to 120 degrees relative to the plane of the body portion.

11. The connecting element of claim 10 wherein the angle is about 60 degrees.

12. The connecting element of claim 10 wherein the body portion defines an axis, and wherein the end portions are twisted along the axis of the body portion at an angle of from 0 to 90 degrees.

13. The connecting element of claim 12 wherein the twist is about 45 degrees.

14. The connecting element of claim 2 wherein the end portions have apertures including an aperture for engaging portions of the first appliance and an aperture for engaging portions of the second appliance.

15. The connecting element of claim 14 wherein the apertures are round.

16. The connecting element of claim 15 wherein the apertures have a diameter of from 1 mm to 4 mm.

17. The connecting element of claim 16 wherein the diameter is about 2 mm.

18. The connecting element of claim 14 wherein at least one of the apertures includes means for preventing swiveling of the connecting element relative to the orthodontic device.

19. The connecting element of claim 18 wherein the preventing means is a shaped aperture for limiting rotation of the connecting element relative to the orthodontic device.

20. The connecting element of claim 19 wherein the shaped aperture slidingly engages the orthodontic device, for promoting lateral and longitudinal movements of the connecting element relative to the orthodontic device.

21. The connecting element of claim 19 wherein the aperture is rectangular in shape.

22. The connecting element of claim 21 wherein the rectangular aperture has a length of from 0.021 inches to 0.1 inches and a width of from 0.017 inches to 0.026 inches.

23. The connecting element of claim 14 wherein the aperture for engaging portions of the first appliance has a first shape, and the aperture for engaging portions of the second appliance has a second shape different from the first shape.

24. The connecting element of claim 14 wherein the aperture for engaging portions of the first appliance has a first size, and the aperture for engaging portions of the second appliance has a second size different from the first size.

25. The connecting element of claim 2 wherein the end portions are rounded.

26. The connecting element of claim 2 wherein at least portions of the connecting element include an outer coating.

27. The connecting element of claim 26 wherein the coating is selected from the group consisting of plastic and rubber.

28. The connecting element of claim 2 wherein the plate forming the connecting element has a size and a shape, and is formed of a material selected to produce a predetermined force between the end portions of the connecting element when attached to and between the first appliance and the second appliance of the orthodontic device.

29. The connecting element of claim 1 wherein the first teeth are associated with a first jaw of the patient and the second teeth are associated with a second jaw of the patient, and wherein the forces developed by the connecting element are sufficient to cause movement of the first teeth relative to the second teeth without causing movement of the first jaw relative to the second jaw.

30. The connecting element of claim 1 wherein a pair of connecting elements are connected between the first teeth and the second teeth, for moving the first teeth relative to the second teeth.

31. The connecting element of claim 30 wherein a first of the connecting elements extends between the first appliance and the second appliance along one side of the first jaw and the second jaw, and a second of the connecting elements extends between the first appliance and the second appliance along an opposing side of the first jaw and the second jaw.

32. The connecting element of claim 31 wherein the first of the connecting elements is a mirror image of the second of the connecting elements.

33. The connecting element of claim 1 wherein the first appliance includes connector means for receiving an end of the connecting element and the second appliance includes connector means for receiving another end of the connecting element.

34. The connecting element of claim 33 wherein the connector means includes a wire for slidingly receiving an aperture formed in the connecting element, and stop means for limiting movement of the connecting element along the wire.

35. The connecting element of claim 34 wherein the connecting element includes means for preventing swiveling of the connecting element relative to the wire of the connector means.

* * * * *